United States Patent [19]

Zysman et al.

[11] Patent Number: 5,149,860
[45] Date of Patent: Sep. 22, 1992

[54] LIPID COMPOUNDS DERIVED FROM SPHINGOSINES, PROCESS FOR PREPARING THESE AND THEIR APPLICATIONS, IN PARTICULAR IN COSMETICS AND IN THE PHARMACY OF SKIN CONDITIONS

[75] Inventors: Alexandre Zysman, Paris; Guy Vanlerberghe, Claye-Souilly; Henri Sebag, Paris, all of France

[73] Assignee: L'Oreal, Paris, France

[21] Appl. No.: 585,653

[22] Filed: Sep. 20, 1990

[30] Foreign Application Priority Data

Sep. 21, 1989 [FR] France .............................. 89 12423

[51] Int. Cl.$^5$ ........................................... C07C 261/00
[52] U.S. Cl. ................................................. 560/160
[58] Field of Search ....................................... 560/160

[56] References Cited

U.S. PATENT DOCUMENTS 4,737,518 4/1988 Nomura ............................. 560/160

FOREIGN PATENT DOCUMENTS 0097059 12/1983 European Pat. Off. .

OTHER PUBLICATIONS

Helvetica Chimica Acta, vol. 71, 1988, pp. 254–361, Herold.
French Search Report of FR 89 12423 (1990).

Primary Examiner—Michael L. Shippen
Attorney, Agent, or Firm—Cushman, Darby & Cushman

[57] ABSTRACT

The invention relates to a lipid compound of formula (I):

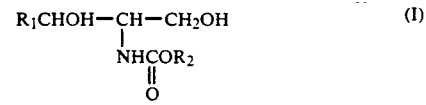

where $R_1$ denotes a $C_{11}$ to $C_{21}$ alkyl or alkenyl radical and $R_2$ denotes a linear or branched $C_8$ to $C_{30}$ hydrocarbon radical, saturated or bearing one or more ethylenically unsaturated bonds, and also to a process for preparing it and to compositions for cosmetic use of pharmaceutical use for skin conditions containing this compound.

4 Claims, No Drawings

LIPID COMPOUNDS DERIVED FROM SPHINGOSINES, PROCESS FOR PREPARING THESE AND THEIR APPLICATIONS, IN PARTICULAR IN COSMETICS AND IN THE PHARMACY OF SKIN CONDITIONS

The present invention relates to new lipid compositions derived from sphingosines, to a process for preparing these and also to their use, in particular for treatment and care of the skin and hair in cosmetics or in the pharmacy of skin conditions.

Exposure of the skin to cold, to the sun and to atmospheres with a low relative humidity, repeated treatments with washing compositions or alternatively contact with organic solvents are factors which, in varying degrees, bring about a noticeable dehydration. The skin appears drier and less supple and the surface of the skin rougher.

Moreover, hair which is too frequently subjected to certain hair-care treatments loses its shiny appearance and can become rough and brittle.

The Applicants have hence investigated compounds which enable these phenomena reflected in a noticeable dehydration to be prevented or corrected, and which restore to the skin its suppleness and surface, and to the hair its sheen and softness.

Thus, the Applicants have discovered new compounds whose constitution may be represented by the following formula:

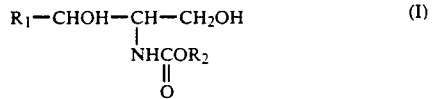

in which:

$R_1$ denotes a $C_{11}$ to $C_{21}$ alkyl or alkenyl radical optionally bearing a hydroxyl group; and $R_2$ denotes a linear or branched $C_8$ to $C_{30}$ hydrocarbon radical, saturated or alternatively bearing one or more ethylenically unsaturated bonds, and preferably denotes an alkyl or alkenyl radical.

The above lipid compounds (I) are, through their structure, very similar to ceramides, which are the preponderant components constituting the intercorneocytic lipids of the stratum corneum. It is generally accepted that they participate in maintaining the integrity of the cutaneous barrier. They are also found, to a lesser extent, in the hair. The compounds (I) according to the invention, which are low melting point waxes, are hence of very special interest for treatment and care of the skin and hair in cosmetics or in the pharmacy of skin conditions, enabling some effects of the noticeable dehydration to be prevented or corrected.

These compounds display, moreover, little tendency to damage the skin or the ocular mucosae, and are well tolerated by cell membranes such as those of erythrocytes.

The new compounds of formula (I) above display emollient and demulcent properties. They are readily solubilized in the fatty phases of cosmetic preparations or pharmaceutical preparations for the skin.

The compounds of formula (I) in which $R_2$ represents a linear chain, which will be referred to hereinafter as compounds (I'), form vesicles in combination with other lipids.

The subject of the present invention is thus the new lipid compounds of formula (I) defined above.

The lipid compounds of formula (I) above result from the condensation of the amine function of a sphingosine, a dihydrosphingosine or a phytosphingosine with an alkyl or alkenyl chloroformate or with an alkyl or alkenyl imidazolide.

Another subject of the present invention hence consists of the process for preparing the compounds of formula (I) which may be represented by the following scheme:

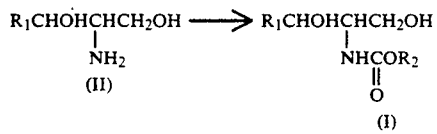

$R_1$ and $R_2$ having the meanings stated above.

The compounds (I) are obtained by reaction of the compounds of formula (II) either with an alkyl or alkenyl chloroformate in solvents such as dimethylformamide or tetrahydrofuran in the presence of a base such as, for example, triethylamine, pyridine, and the like, or with an alkyl or alkenyl imidazolide, isolated or prepared in situ, for example by the reaction of a fatty alcohol with carbonyl diimidazole.

The alkyl or alkenyl chloroformates are commercial products.

The alkyl or alkenyl imidazolides, prepared in situ or isolated in the pure state, are synthesized according to the methods described by H. A. STAAB in Angew. Chem. International Edit. vol. 1 (1962), No. 7, p. 351.

For the preparation of the compound (I) of the invention, the hydrochloride of the compound (II) may also be used. This hydrochloride is then solubilized, preferably in tetrahydrofuran with the addition of 10% of water. The base (II) is then liberated in situ with an excess of a hydrogen carbonate.

The compounds (II) are known compounds. Their synthesis has been described, in particular, by D. SHAPIRO in "Chemistry of sphingolipids", HERMANN, Paris (1969).

When $R_1$ denotes an alkenyl radical, the compounds (II) are sphingosines.

When $R_1$ denotes an alkyl radical, the compounds (II) are dihydrosphingosines. They may be prepared, in particular, from methyl or ethyl 2-acetamido-3-oxoalkanoate, as described in "Chemistry of sphingolipids", p. 32.

When $R_1$ denotes a hydroxylated alkyl radical, the compounds (II) are phytosphingosines. They may be prepared, inter alia, from sphingosines according to the scheme described by B. Weiss in Biochemistry, 4, p. 686 (1965).

The processes for the synthesis of sphingosines, dihydrosphingosines and phytosphingosines described above lead to racemic mixtures It is possible to obtain these compounds in the form of pure enantiomers by carrying out a resolution of the racemate described, for example, by SHAPIRO in the abovementioned article, on page 99.

Pure enantiomers may also be synthesized directly. A very large number of processes have been described, such as, for example, by R. SCHMIDT in "Tetrahedron Letters", vol. 27, No. 4, pages 481-84 (1986), by B. BERNET in the same journal, vol. 24, No. 49, pages 5491-5494 (1983) or alternatively by MAKOTO KISO in "Carbohydrate Research", 158 (1986), pages 101-111, and the like.

Some compounds (II) are commercial compounds, such as D-sphingosine sold by the company Sigma.

The compounds according to the invention can receive various applications, in particular as waxy constituents in cosmetic compositions and pharmaceutical compositions for the skin. The compounds of formula (I') possess, in addition, the property of forming vesicles in combination with other lipids when they are dispersed in water.

The subject of the present invention is hence the use of the lipid compositions of formula (I) as waxy constituents in emulsions or dispersions or in lotions. The subject of the invention is also the use of the compounds of formula (I'), combined with other lipids, for the formation of lipid spherules.

The subject of the present invention is also compositions for cosmetic use or pharmaceutical use for skin conditions, containing a compound of formula (I).

The compositions according to the invention may be presented in the form of emulsions (milk or cream), aqueous-alcoholic, oily or oleoalcoholic lotions, or gels, dispersions or solid sticks.

According to the invention, the compounds of formula (I) represent 0.05% to 20%, and preferably 0.1 to 10%, of the total weight of the composition.

The compositions are, for example, emollient lotions, milks or creams, lotions, milks or creams for skin or hair care, makeup-removal creams or milks, makeup foundation bases, antisun lotions, milks or creams, artificial tanning lotions, milks or creams, shaving creams or foams, or after-shave lotions.

These compositions may also be presented in the form of sticks for the lips, intended either for coloring them or for preventing chapping, or makeup products for the eyes or makeup and foundations for the face.

When the compositions according to the invention are presented in the form of water-in-oil or oil-in-water type emulsions, the fatty phase consists essentially of a mixture of compound of formula (I) with at least one oil, and optionally another fat.

The fatty phase of the emulsions can constitute 5 to 60% of the total weight of the emulsion.

The aqueous phase of the said emulsions preferably constitutes 30 to 85% of the total weight of the emulsion.

The proportion of the emulsifying agent can be between 1 and 20%, and preferably between 2 and 12%, of the total weight of the emulsion.

When the compositions of the invention are presented in the form of oily, oleoalcoholic or aqueousalcoholic lotions, they can constitute, for example, antisun lotions containing a screening agent absorbing UV rays or demulcent lotions for the skin or hair; the oily lotions can, in addition, constitute foaming oils containing an oil-soluble surfactant, bath oils, and the like.

Among the main adjuvants capable of being present in the compositions according to the invention, there may be mentioned fats such as mineral, animal or vegetable oils or waxes, fatty acids, fatty acid esters such as fatty acid triglycerides having 6 to 18 carbon atoms, fatty alcohols; emulsifiers such as polyglycerol alkyl ethers or oxyethylenated fatty alcohols; and solvents such as lower monohydric alcohols or polyhydric alcohols containing from 1 to 6 carbon atoms, or alternatively water.

Especially preferred monohydric or polyhydric alcohols are selected from ethanol, isopropanol, propylene glycol, glycerol and sorbitol.

By way of fats, among the mineral oils, liquid paraffin may be mentioned; among animal oils, whale, seal, menhaden, halibut-liver, cod, tunny, turtle, neat's-foot, horse's-foot, sheep-foot, mink, otter and marmot oil, and the like; and among vegetable oils, almond, groundnut, wheat-germ, olive, maize-germ, jojoba, sesame, sunflower, palm, nut, shea, shorea, macadamia and blackcurrant-pip oil, and the like.

Among fatty acid esters, esters of saturated or unsaturated $C_{12}$ to $C_{22}$ acids and of lower alcohols such as isopropanol or glycerol, or of saturated or unsaturated, linear or branched $C_8$ to $C_{22}$ fatty alcohols, or alternatively of $C_{10}$ to $C_{22}$ 1,2-alkanediols, may be used.

Vaseline, paraffin wax, lanolin, hydrogenated lanolin, tallow, acetylated lanolin and silicone oils may also be mentioned as fats.

Among waxes, Sipol wax, lanolin wax, beeswax, candelilla wax, microcrystalline wax, carnauba wax, spermaceti, cocoa butter, shea butter, silicone waxes, hydrogenated oils solid at 25° C., sucroglycerides and Ca, Mg and Al oleates, myristates, linoleates and stearates may be mentioned.

Among fatty alcohols, lauryl, cetyl, myristyl, stearyl, palmityl and oleyl alcohols and GUERBET alcohols such as 2-octyldodecanol, 2-decyltetradecanol or 2-hexyldecanol may be mentioned.

By way of emulsifiers, among polyoxyethylenated fatty alcohols, there may be mentioned lauryl, cetyl, stearyl and oleyl alcohols containing from 2 to 20 moles of ethylene oxide, and among polyglycerol alkyl ethers, $C_{12}$-$C_{18}$ alcohols containing from 2 to 10 moles of glycerol.

It can also be useful to employ thickeners such as cellulose derivatives, polyacrylic acid derivatives, guar or carob gum or xanthan gum.

The composition according to the invention can also contain adjuvants customarily used in cosmetics or in the pharmacy of skin conditions, and in particular hydrating and demulcent products, products for the treatment of skin conditions, sunscreening agents, germicides, colorings, preservatives, fragrances and propellants.

When the compositions according to the invention are dispersions, they can be dispersions of compounds of formula (I) in water in the presence of a surfactant, or alternatively aqueous dispersions of lipid spherules consisting of organized molecular layers containing an encapsulated aqueous phase, these layers consisting of at least one compound of formula (I') combined with at least one other lipid compound.

To this end, as a lipid compound, there may be mentioned long-chain alcohols and diols, sterols such as cholesterol, phospholipids, cholesteryl sulphate and phosphate, long-chain amines and their quaternary ammonium derivatives, dihydroxyalkylamines, polyoxyethylenated fatty amines, esters of long-chain amino alcohols, their salts and quaternary ammonium derivatives, phosphoric esters of fatty alcohols such as sodium dicetyl phosphate, alkyl sulphates such as sodium cetyl sulphate or alternatively lipids of the type described in French Pat. Nos. 2,315,991, 1,477,048 and 2,091,516, or in International Patent Application WO 83/01 571.

Lipids containing a long, saturated or unsaturated, linear or branched lipophilic chain containing 12 to 30 carbon atoms, for example an oleic, lanolic, tetradecyl, hexadecyl, isostearyl, lauric or alkylphenyl chain, can, for example, be used as other lipids. The hydrophilic group of these lipids can be an ionic or nonionic group. By way of nonionic groups, groups derived from polyethylene glycol may be mentioned. By way of an ionic group, a group derived from an amphoteric, anionic or cationic compound can advantageously be used. As lipids forming the lamellar phase, polyglycerol ethers such as those described in French Patents 1,477,048, 2,091,516, 2,465,780 and 2,482,128 can also be advantageously used.

Other lipids described in International Patent Application No. WO 83/01,571 as being capable of use for the formation of liposomes are glycolipids such as lactosylceramide, galactocerebroside, gangliosides and trihexosylceramide, as well as phospholipids such as phosphatidyl glycerol and phosphatidylinositol.

The subject of the present invention is hence also a dispersion of lipid spherules consisting of organized molecular layers of compound(s) of formula (I') and lipid defined above, containing an aqueous phase to be encapsulated.

The continuous phase of the dispersion which surrounds the spherules is an aqueous phase.

The spherules in dispersion are between 0.1 μm and 5 μm in diameter.

The aqueous phase encapsulated in the spherules can be water or an aqueous solution of active substance, and in this case is preferably isoosmotic with respect to the continuous phase of the dispersion.

The spherules may be obtained, in particular, according to the process described in French Patent 2,315,991, according to which a dispersion of spherules consisting of organized molecular layers containing an aqueous phase to be encapsulated is prepared by bringing into contact, on the one hand one or more lipid compound(s) of the formula (I') combined with one or more lipid(s) defined above, and on the other hand the aqueous phase to be encapsulated in the spherules, agitating to effect mixing and obtain a lamellar phase, then adding a dispersion liquid in an amount greater than the amount of lamellar phase obtained and shaking vigorously for a period ranging from 15 minutes to 3 hours approximately.

The weight ratio of the aqueous phase to be encapsulated to the compound(s) of formula (I') combined with the lipids forming the lamellar phase is preferably between 0.1 and 3.

The weight ratio of the aqueous dispersion phase which is added to the lamellar phase which is dispersed is preferably between 2 and 100, the dispersion phase and the aqueous phase to be encapsulated preferably being isoosmotic.

The agitation is carried out by means of a shaker. The process is preferably carried out at a temperature of between 30° and 120° C.

Another preparation process can consist in using the process designated REV (reverse-phase evaporation vesicle) described in Proc. Natl. Acad. Sci. USA., Vol. 75, No. 9, pages 4194–4198 (1978), by SZOKA and PAPAHADJOPOULOS.

The active substances capable of being encapsulated in the aqueous phase can be substances of pharmaceutical or nutritional interest, or substances having cosmetic activity.

The substances having cosmetic activity can be products intended for skin and hair care, such as, for example, humectants such as glycerol, sorbitol, pentaerythritol, inositol or pyrrolidonecarboxylic acid and its salts; artificial tanning agents such as dihydroxyacetone erythrulose, glyceraldehyde and γ-dialdehydes such as tartraldehyde, these compounds optionally being combined with colorings; water-soluble sunscreen agents; antiperspirants, deodorants, astringents, freshening, toning, healing, keratolytic and depilatory products and perfumed waters; extracts of animal or plant tissues such as proteins, polysaccharides and amniotic fluid; water-soluble colorings; antidandruff agents, antiseborrhoeic agents and oxidizing agents such as bleaching agents, for example hydrogen peroxide; and reducing agents such as thioglycolic acid and its salts.

As pharmaceutical active substances, vitamins, hormones, enzymes such as superoxide dismutase, vaccines, anti-inflammatories such as hydrocortisone, antibiotics, bactericides and cytotoxic or antitumour agents may be mentioned.

Various adjuvants such as opacifiers, gelling agents, aromas, fragrances or colorings may also be added to the dispersions of spherules according to the invention.

The dispersions of lipid spherules according to the invention have the advantage of transporting hydrophilic active substances which are thus masked and protected from the various agents causing adverse changes: oxidizing agents and, more generally, compounds reactive towards the encapsulated active substances. The penetration and binding of the active substances may be adjusted by varying the size of the spherules and their electrical charge. The action of these active substances can thus also be delayed (retard effect). Finally, as a result of the use of the lipids (I') according to the invention and of combined active substances, it is possible to obtain a beneficial action specific to the active substance used and at the same time a softening action, which is especially advantageous in the case of treatment of the skin and hair.

The subject of the present invention is hence also the use in cosmetics of an aqueous dispersion of spherules consisting of organized molecular layers of lipid compounds (I') combined with other lipids, containing an aqueous phase to be encapsulated, especially for the treatment of the skin and hair.

The subject of the invention is also the use of such a dispersion of lipid spherules in the pharmacy of skin conditions or in the food industry.

The present invention will be better illustrated by the following non-limiting examples.

EXAMPLE 1

1st step

Preparation of the compound (II) with $R_1 = C_{15}H_{31}$: 1,3-dihydroxy-2-aminooctadecane hydrochloride (erythro/threo mixture)

Methyl 2-acetamido-3-oxooctadecanoate (100 g) equivalent to 0.27 mol) is suspended in 1 liter of absolute ethanol. The temperature of the reaction medium is brought to below 0° C. At this temperature, 30.7 g (0.8 mol) of sodium borohydride are added in three portions and stirring is maintained at this temperature for 3 hours. The reaction medium is then brought to reflux of the solvent for 3 hours. After cooling to room temperature, 140 cm³ of concentrated hydrochloric acid are added and the reaction medium is again brought to reflux for 3 hours. This medium is filtered while still hot on a glass sinter. The filtrate is concentrated to dryness under reduced pressure.

The solid obtained is recrystallized in 300 cm³ of heptane/ethyl acetate (90:10) solvent mixture. 88 g of a white solid are isolated, the acid value of which, measured in ethanol with N/10 sodium hydroxide solution, is 2.99 meq/g.

The ¹³C NMR spectrum of this solid is in agreement with the expected structure

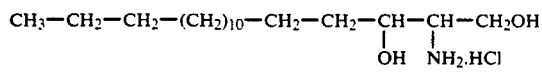

The product is, in point of fact, dihydrosphingosine hydrochloride in the form of an erythro/threo racemic mixture.

2nd step

Preparation of the compound (I) in which $R_2$=2-ethylhexyl 20 g ($5.92 \times 10^{-2}$ mol) of dihydrosphingosine hydrochloride, prepared above, are solubilized at room temperature in 110 cm³ of tetrahydrofuran with the addition of 11 cm³ of water.

11.41 g ($5.92 \times 10^{-2}$ mol) of 2-ethylhexyl chloroformate, solubilized in 36 cm³ of tetrahydrofuran, are added to this solution.

20.11 g (0.237 mol) of sodium hydrogen carbonate are added to this reaction mixture and the latter is left stirring at room temperture overnight.

500 cm³ of water are then added. After separation of the two phases when settling has taken place, the upper phase is isolated and the solvent is removed by distillation under partial vacuum. 22 g of a wax of m.p. 50° C. are collected, the ¹³C NMR spectrum of which confirms the expected structure (erythro/threo mixture), which is as follows:

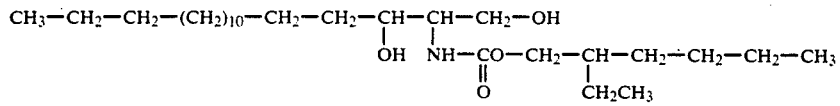

| | Elemental analysis: | |
|---|---|---|
| | Calculated | Measured |
| C | 70.85 | 70.70 |
| H | 12.11 | 12.08 |
| N | 3.06 | 3.09 |

EXAMPLE 2

Preparation of the compound (I) in which $R_2$=cetyl ($C_{16}H_{33}$)

16.9 g (0.05 mol) of dihydrosphingosine hydrochloride, prepared as in Example 1, are solubilized at room temperature in 200 cm³ of tetrahydrofuran with the addition of 20 cm³ of water. 15.2 g (0.05 mol) of cetyl chloroformate, solubilized in 50 cm³ of tetrahydrofuran, are added to this solution. 17 g (0.2 mol) of sodium hydrogen carbonate are added to this reaction mixture and stirring is maintained at room temperature overnight. 1 liter of water is then added with stirring. The precipitate formed is isolated by filtration on a glass sinter. After drying, 26.4 g of a white solid of m.p. 82° C., corresponding to the following formula:

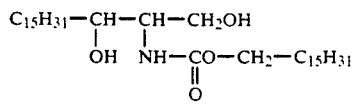

are obtained.

The ¹³C NMR spectrum confirms the expected structure (erythro/threo mixture)

| | Elemental analysis: | |
|---|---|---|
| | Calculated | Measured |
| C | 73.76 | 73.10 |
| | | 73.09 |
| H | 12.56 | 12.60 |
| | | 12.63 |
| N | 2.46 | 2.40 |
| | | 2.40 |

EXAMPLE 3

1st step

Preparation of the compound of (II) with $R_1=C_{15}H_{31}$: 1,3-dihydroxy-2-aminooctadecane (erythro form)

Methyl 2-acetamido-3-oxooctadecanoate (218 g, equivalent to 0.59 mol) is suspended in 1090 cm³ of absolute ethanol. 65.4 g (1.73 mol) of sodium borohydride are added in a single portion at 0° C. Stirring is maintained at this temperature for 3 hours, and then for a further 4 hours at room temperature. Finally, the mixture is heated to reflux of the solvent for 6 hours. The solvent is then removed under reduced pressure and the residue is taken up with 600 cm³ of ethyl acetate and 500 cm³ of water. The two phases are separated after settling has taken place at 60° C. The upper phase is filtered through paper and then left overnight at 4° C.

178 g of white solid, corresponding to 2-acetylamino-3-hydroxyoctadecanol, are isolated by filtration on a glass sinter and after drying.

158 g of the above compound are dissolved in 1054 cm³ of methanol including 10% of water containing 129.1 g of potassium hydroxide. The reaction medium is brought to reflux for 6 hours and then filtered through paper while hot. The filtrate is made up with 300 cm³ of water and left at 4° C. overnight. The solid formed is isolated by filtration on a glass sinter. 145 g of 2-amino-3-hydroxyoctadecanol or dihydrosphingosine are thereby obtained in pure erythro form.

The ¹³C NMR spectrum is in agreement with the expected structure:

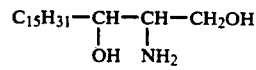

2nd step

Preparation of the compound (I) with $R_2$=phytyl ($C_{20}H_{39}$)

a) Preparation of phytol imidazolide 18 g (0.11 mol) of carbonyldiimidazole are solubilized in 180 cm³ of dichloromethane, and 29.6 g (0.1 mol) of phytol, solubilized in 30 cm³ of the same solvent, are then added. The reaction mixture is then stirred overnight at room temperature. After dilution of the medium with 200 cm³ of dichloromethane, it is washed three times with 100 cm³ of water. The organic phase is dried over sodium sulphate. After removal of the solvent under reduced pressure, 35.2 g of phytol imidazolide, which takes the form of an oil, are isolated.

It corresponds to the formula below:

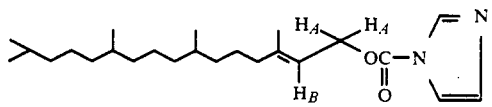

The structure is confirmed by the ¹H NMR spectrum.

b) Preparation of the compound (I) with $R_2$=phytyl 25 g (0.055 mol) of imidazolide prepared above are solubilized in 100 cm³ of tetrahydrofuran and added to a solution of the same solvent containing 14.4 g (0.048 mol) of dihydrosphingosine, prepared according to the 1st step above. The reaction medium is stirred at room temperature overnight. The solvent is removed under reduced pressure. The residue obtained is taken up with 300 cm³ of dichloromethane and washed four times with 100 cm³ of water.

After drying of the organic phase over sodium sulphate followed by removal of the solvent under reduced pressure, a residue is obtained, which is subjected successively to two HPLC separations on silica (MERCK KIESELGEL 60). The first separation is performed with a dichloromethane/methanol (98:2) mixture, and the second with a heptane/ethyl acetate (6:4) mixture. Three fractions A, B and C weighing 2, 1.5 and 2.5 g, respectively, which take the form of waxes of m.p. <60° C., are isolated.

Fraction A

This corresponds to the formula:

$C_{15}H_{31}$—CH—CH—CH$_2$OH      trans isomer
         |    |
        OH  NH—CO

|   | Elemental analysis: | |
|---|---|---|
|   | Calculated | Measured |
| C | 75.06 | 75.14 |
| H | 12.44 | 12.46 |
| N | 2.24 | 2.29 |

The ¹³C NMR spectrum confirms the expected structure.

Fraction C

This corresponds to the formula:

$C_{15}H_{31}$—CH—CH—CH$_2$OH     cis isomer

The ¹³C NMR spectrum confirms the expected structure. Elemental analysis:

|   | Elemental analysis: | |
|---|---|---|
|   | Calculated | Measured |
| C | 75.06 | 75.08 |
| H | 12.44 | 12.47 |
| N | 2.24 | 2.17 |

Fraction B

On the basis of thin-layer chromatography and on the basis of NMR, this corresponds to a mixture of the above cis and trans isomers.

EXAMPLE 4

1st step

Preparation of 2-decyltetradecyl imidazolide 10.5 g (0.065 mol) of carbonyldiimidazole are solubilized in 105 cm³ of dichloromethane. 20 g (0.057 mol) of 2-decyltetradecanol, diluted in 20 cm³ of dichloromethane, are then added to this solution. The reaction medium is left overnight at room temperature with stirring. 200 cm³ of dichloromethane are then added and the reaction medium is washed three times with 100 cm³ of water. After concentration, 26 g of an oil are isolated, equivalent to a quantitative yield of 2-decyltetradecyl imidazolide, corresponding to the formula:

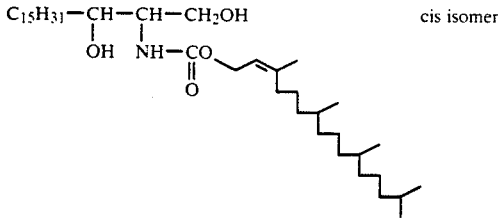

The ¹H NMR spectrum confirms the expected structure.

2nd step

Preparation of the compound (I) with $R_2$=2-decyltetradecyl 14.5 g (0.055 mol) of imidazolide prepared above are solubilized in 100 cm³ of tetrahydrofuran and added to a solution of the same solvent containing 15.5 g (0.05 mol) of dihydrosphingosine, prepared according to the 1st step of Example 3. The reaction medium is stirred at room temperature overnight and the solvent is then evaporated off under reduced pressure. The oil obtained is subjected to a purification by HPLC on a column of MERCK KIESELGEL 60 silica with a dichloromethane/methanol (98:2) mixture as eluent.

13 g of white solid of m.p. 72° C., and corresponding to the formula:

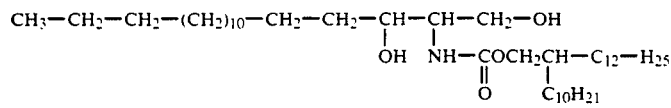

are isolated. It is the pure erythro isomer.

The $^{13}$C NMR spectrum confirms the expected structure.

| | Elemental analysis: | |
|---|---|---|
| | Calculated | Measured |
| C | 75.71 | 75.74 |
| H | 12.85 | 12.84 |
| N | 2.05 | 2.08 |

EXAMPLE I

Skin care cream

A cream having the following composition was prepared:

| | |
|---|---|
| Compound of Example 4 | 3 g |
| Glyceryl stearate | 2 g |
| TWEEN 60 (sorbitan monostearate containing 20 mol of ethylene oxide) | 1 g |
| Cetyl alcohol | 0.5 g |
| Stearic acid | 1.4 g |
| Triethanolamine | 0.7 g |
| CARBOPOL 940 (crosslinked polyacrylic acid) neutralized with triethanolamine | 0.4 g |
| Liquid fraction of shea grease | 12 g |
| Synthetic perhydrosqualene | 12 g |
| Antioxidant | 0.05 g |
| Fragrance | 0.5 g |
| Preservative | 0.3 g |
| Water qs | 100 g |

This cream (oil-in-water emulsion) is prepared in the following manner:

The CARBOPOL 940, neutralized with triethanolamine, is added to a portion of the water (85 to 90%) and the mixture is heated to 75°-80° C. The fatty phase (glyceryl stearate, TWEEN 60, stearic acid, compound of Example 4, cetyl alcohol, liquid fraction of shea grease, perhydrosqualene, antioxidant), brought to the same temperature, to which the triethanolamine has been added at the end, is then added with agitation. After 10 minutes' agitation, the preservative, dissolved in the remainder of the water, is added. After a further 10 minutes, the fragrance is added, agitation is then stopped and the mixture is cooled to room temperature (25° C.).

EXAMPLE II

Identical to Example I, but the compound of Example 4 is replaced by 2 g of compound of Example 3.

EXAMPLE III

Body milk

A milk having the following composition was prepared:

| | |
|---|---|
| Compound of Example 3 | 3 g |
| Sorbitan monoisostearate | 5 g |
| Microcrystalline wax | 1 g |
| Liquid paraffin | 15 g |
| Maize-germ oil | 4 g |
| Mixture* of esters of $C_8$-$C_{10}$ fatty acids and $C_{12}$-$C_{18}$ fatty alcohols | 1 g |
| Gel** of modified montmorillonite and neutral oil (triglycerides of caprylic and capric acids) | 5 g |
| Propylene glycol | 3 g |
| Antioxidant | 0.1 g |
| Preservative | 0.3 g |
| Water qs | 100 g |

*Marketed by HENKEL under the tradename "CETIOL-LC DEO"
**Marketed by DYNAMIT NOBEL under the tradename "MYGLYOL-GEL"

This body milk is prepared in a manner similar to that described in Example I.

EXAMPLE IV

Hydrating cream

| | |
|---|---|
| Compound of Example 1 | 5 g |
| Glyceryl stearate | 2 g |
| TWEEN 60 | 1 g |
| Stearic acid | 1.4 g |
| Triethanolamine | 0.7 g |
| CARBOPOL 940 (neutralized with triethanolamine | 0.2 g |
| Sweet almond oil | 3 g |
| Liquid paraffin | 8 g |
| Antioxidant | 0.05 g |
| Preservative | 0.3 g |
| Water qs | 100 g |

This cream is prepared in a manner similar to that described in Example I.

EXAMPLE V

Hydrating dispersion

| | |
|---|---|
| Compound of Example 2 ($R_2$ = cetyl) | 1 g |
| Cholesterol | 1.5 g |
| Sodium dicetyl phosphate | 2.5 g |
| Glycerol | 3 g |
| Preservative | 0.15 g |
| Water qs | 100 cc |

The lipids and also the preservative are solubilized in 950 cm$^3$ of a dichloromethane/methanol (2:1) solvent mixture. The solution is then evaporated to dryness. The water containing the glycerol is added dropwise and with agitation to the lipid film while heating to 90° C.

A dispersion of vesicles of milky appearance, used for hydrating the skin, is obtained.

What is claimed is:

1. Lipid compound of the formula:

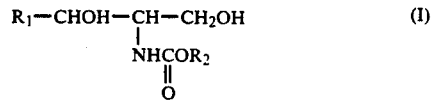

in which $R_1$ denotes a $C_{11}$ to $C_{21}$ alkyl or alkenyl radical optionally bearing a hydroxy group, and $R_2$ denotes a linear or branched $C_8$ to $C_{30}$ hydrocarbon radical, saturated or bearing one or more ethylenically unsaturated bonds.

2. Compound according to claim 1, wherein $R_1$ bears a hydroxyl group.

3. Compound according to claim 1, wherein $R_2$ is an alkyl or alkenyl radical.

4. Compound according to claim 1, wherein $R_1$ denotes a pentadecyl radical and $R_2$ is selected from 2-ethylhexyl, cetyl, phytyl and 2-decyltetradecyl radicals.

* * * * *